US006996497B2

(12) United States Patent
Floyd et al.

(10) Patent No.: US 6,996,497 B2
(45) Date of Patent: Feb. 7, 2006

(54) METHOD OF EVALUATING LOGS TO PREDICT PROPERTIES OF LUMBER OR VENEER PRODUCED FROM THE LOGS

(75) Inventors: Stanley L. Floyd, Enumclaw, WA (US); Y. Carol Miltimore, Enumclaw, WA (US); Chih-Lin Huang, Bellevue, WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

(21) Appl. No.: 10/013,644

(22) Filed: Nov. 13, 2001

(65) Prior Publication Data

US 2003/0093241 A1    May 15, 2003

(51) Int. Cl.
  *G06F 7/04*    (2006.01)
(52) U.S. Cl. .................. 702/181; 702/170; 702/186; 702/189
(58) Field of Classification Search .............. 702/34, 702/35, 36, 38, 40, 42, 43, 155, 157, 158, 702/170, 181, 189, 127, 146, 151, 186; 428/305.5; 144/350; 73/597
See application file for complete search history.

(56) References Cited

U.S. PATENT DOCUMENTS

| 4,301,202 A | * | 11/1981 | Kohn ..................... 428/50 |
| 5,652,065 A | * | 7/1997 | Park et al. ............... 428/537.1 |
| 5,960,104 A | * | 9/1999 | Conners et al. .......... 382/141 |
| 6,026,689 A | | 2/2000 | Snyder et al. ............. 73/602 |
| 6,305,224 B1 | * | 10/2001 | Stanish et al. ............ 73/597 |
| 6,598,477 B2 | * | 7/2003 | Floyd ........................ 73/597 |
| 6,889,551 B2 | * | 5/2005 | Andrews et al. .......... 73/597 |

FOREIGN PATENT DOCUMENTS

WO    WO 00/12230    3/2000

OTHER PUBLICATIONS

Wagner F. G. and F. W. Taylor. Impact of log sweep on warp in southern pine structural lumber. *Forest Products Journal* 45(2): 59-62 (1995).

* cited by examiner

*Primary Examiner*—Marc S. Hoff
*Assistant Examiner*—Felix Suarez

(57) ABSTRACT

A method is disclosed for evaluating logs to predict structural properties and/or warp tendency of lumber or veneer that might be produced from a given log. The method can be used in a forest stand, sorting yard or merchandiser, on-line in a sawmill, or at other locations along the route from forest to mill. It enables decisions whether a log should be directed to a sawmill for lumber manufacture or for other applications such as timbers, veneer, or pulp chips. Log taper has been found to correlate with both stiffness and warp propensity of lumber cut from a given log. A high amount of taper leads to warped lumber and low stiffness lumber or veneer. The correlation with taper is highest if it is measured over the full stem length of the harvested log, before it is bucked to sawmill size or veneer blocks. Other geometric features of the log, such as sweep or cross section irregularity, can be combined with taper in a multivariate regression equation to increase accuracy of prediction. This can readily be accomplished in a conventional scanner used in a sort yard or sawmill.

18 Claims, 10 Drawing Sheets

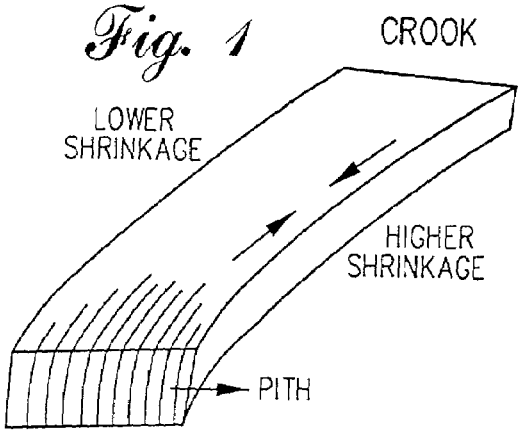
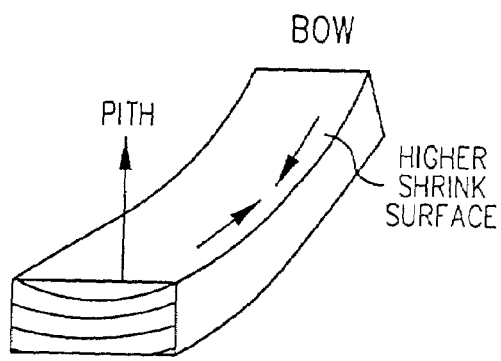
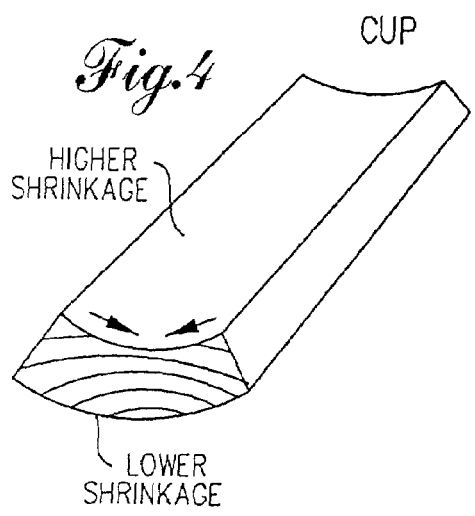
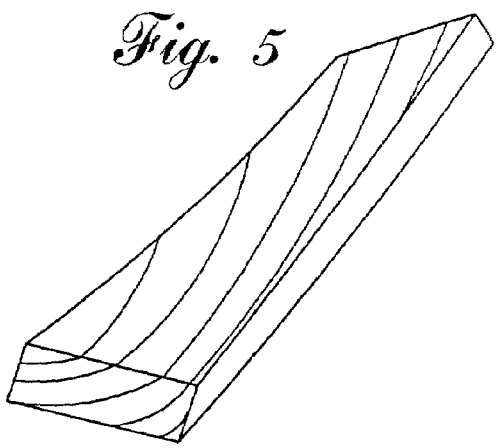
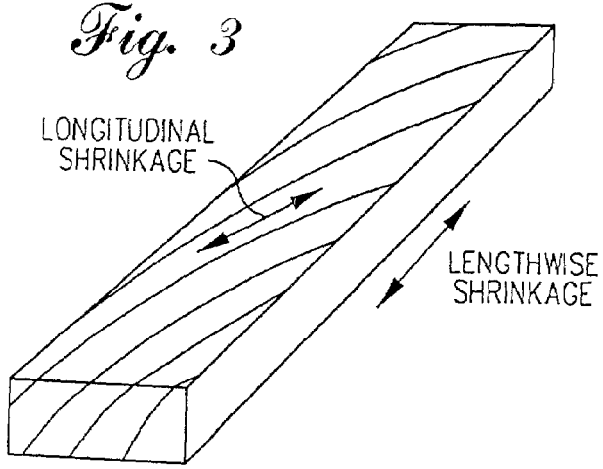

METHOD OF EVALUATING LOGS TO PREDICT PROPERTIES OF LUMBER OR VENEER PRODUCED FROM THE LOGS

The present invention is directed to a method for evaluating logs to predict structural strength and/or warp tendency of lumber or veneer that might be produced from a given tree or log. The method can be used in a forest stand, in a sorting yard or merchandiser, on-line in a sawmill, or at other locations along the route from forest to mill. It enables decisions whether a log should be directed to a sawmill for lumber manufacture or for other applications such as timbers, veneer, or pulp chips.

BACKGROUND OF THE INVENTION

The majority of the available old growth softwood forests in the world have now been harvested. This wood has been replaced in many areas of the world by trees grown on intensively managed plantations or "tree farms". Over the years nurseries producing seed for plantation trees have used intensive genetic selection to improve such heritable traits as rapid growth, straightness of stem, reduced limb diameter, and other desirable characteristics. Most growth cycles now include one or more fertilizations. Plantation trees are also usually thinned and may be pruned one or more times. While plantations now provide a dependable supply of wood for lumber and pulp, the transition from old growth to plantation wood has seen a significant change in size and characteristics of the wood supplied to the mills. Depending on the species and growth locale, plantation trees for saw logs are usually harvested on a 20–50 year growth cycle. The various pine species are usually harvested 20–30 years after planting and typically produce logs having a butt diameter about 30–60 cm.

It is the nature of most conifer species to produce wood having so-called juvenile characteristics during the first 10–15 years of their growth. This juvenile wood is characterized by thinner cell (tracheid) walls and a higher microfibril angle in the tracheid walls. One characteristic of juvenile wood is reduced density. Another, attributed to the greater microfibril angle, is greater longitudinal shrinkage on drying. Density increases as wood is laid down at greater distances from the pith and the microfibril angle decreases until wood laid down after about 12–15 years growth has acquired "adult" properties. Under normal conditions, density and microfibril angle then remain essentially constant during the remaining years of the tree's growth. This difference in properties radially across the logs can affect the strength and other properties of lumber sawn from the trees. Microfibril angle and density are known to correlate directly with modulus of elasticity (stiffness). Further, the difference in longitudinal shrinkage from pith to outer wood can be responsible for warp of lumber produced from the logs, particularly the defects known as bow and crook.

Various means have been proposed to overcome the above problems. For example, U.S. Pat. No. 6,001,452 to Bassett et al. shows a composite lumber product in which the denser wood from the outer portions of the tree is selectively located in a composite lumber product to improve bending strength. Published PCT application WO 00/12230 to Stanish et al. describes a method of predicting warp potential by estimating lengthwise shrinkage rates and measuring grain angle of lumber.

Snyder et al., in U.S. Pat. No. 6,026,689, describe a method of estimating modulus of elasticity of wood (MOE) in a log by impacting the log with a pneumatic hammer and measuring velocity of the resulting stress wave. Related technology is described in PCT Applications WO 00/11467 and WO 01/09603 and British Patent 1,244,699. In general, low stress wave velocity correlates with lower modulus wood. Average stress wave velocity has also been used in an attempt to predict warp in lumber but correlation has been so poor as to not be generally useful.

The method described by Stanish et al. is more applicable to cut lumber than to raw logs and is relatively complex. It would be extremely useful if there was a simple method of predicting product properties early so that logs could be allocated to uses that would maximize return. As one example, logs having high stiffness but showing a tendency to produce warp prone lumber might be allocated to veneer for production of parallel laminated lumber. Logs having lower stiffness and prone to production of warp prone lumber might be used for solid sawn timbers or plywood. Alternatively, other uses such as particle, flake, or oriented strand boards or chips for wood pulp would be possible.

In a study of 75 small pine logs, F. G. Wagner and F. W. Taylor suggest a possible relationship between log sweep with bow or crook of finished lumber (Impact of log sweep on warp in southern pine structural lumber, *Forest Products Journal*, 45(2): 59–62 (1995)). Other than obvious defects such as limb stubs, overall log geometry has apparently not been seriously considered as a predictor of product properties.

The present invention is directed to a simple procedure that makes a reliably predictable estimation of warp propensity or product structural properties from logs both possible and fully compatible with existing operations at a sort yard or in an integrated sawmill.

SUMMARY OF THE INVENTION

The present invention is a method that enables prediction of structural and warp properties that might be expected in lumber or veneer produced from a standing tree, a felled tree stem, or a given log cut from the stem. The term "structural properties" generally refers to all the stiffness (modulus of elasticity) or strength values of the wood. The method includes determination of the external geometric configuration of the log that may be done by known scanners. Determination of any taper in the log is a critical to the invention. Data relating to lack of longitudinal axis linearity (sweep), or deviation from cross section circularity, are also useful but are not critical. Data from the taper measurement may be used directly to predict wood stiffness and warp propensity. Alternatively, taper along with data from other geometric measurements may be included in a multivariate regression equation that can predict with even greater accuracy the warp tendency or stiffness of lumber that might be milled from the log. In many cases, such as at sort yards or log merchandisers, the necessary taper and other geometric data are routinely determined before the log ever enters the sawmill. The taper and other geometric data can be programmed into the existing computers associated with log scanners to determine what type of product should be produced from the log. If a high tendency for warp is indicated, the log might be sawn into timbers rather than dimension lumber. Alternatively, it could be directed to production of veneer, wood composites, or chips for pulp manufacture.

Log scanners are available from a number of manufacturers. These are in common use at merchandisers and in sawmills and plywood mills. Among other benefits, they can determine the best orientation of the log as it is presented to the primary breakdown saws. Scanners also typically determine optimum settings for primary breakdown and secondary processing saws in order to obtain maximum product value. In the case of plywood, scanners determine the optimum centers for chucking the lathe block.

While there are differences in method of operation and in the data determined, most log scanners will make a multiplicity of circumferential scans along the length of the log to determine such properties as large and small end diameters, cross sectional shape, and sweep. Sweep may be in one or more planes and this will be detected by the scanner. These scans may sample location of a hundred or more points at each of successive log circumferences to determine cross sectional configurations. These scans are positioned orthogonal to a longitudinal reference line generally parallel to the log being measured. The circumferential configurations are indicative of the log cross sections and their displacement from the reference line at the scan location. Successive scans may be from about 1–30 cm apart. These geometric measurements may be readily digitized and precisely define the shape of the log. The resulting data can be readily manipulated by an associated computer to automatically program downstream manufacturing decisions.

Using a sample population of logs, a regression equation would typically be determined to set up the relationship between taper and predicted properties for each species and general geographic area where the trees are grown. A representative group of trees, generally at least about 10 and preferably 50 or more, are examined for taper and other geometric measurements. These trees are then sawn or peeled conventionally except that the lumber or veneer from each tree is marked so that its source tree is known. After drying and subsequent finishing operations any observed warp of the lumber is measured. This warp can then be related to the earlier measured properties of the tree. Similarly, stiffness of the lumber or veneer sample can be nondestructively determined by conventional means. The regression equation may relate taper to structural properties, especially stiffness (modulus of elasticity), or to predicted warp propensity. Inclusion of other geometric parameters relating to log sweep or cross sectional characteristics in the regression equation can further improve prediction accuracy.

As was noted earlier, stress wave velocity has been used in the past as a predictor of stiffness. However, the present method using taper measurement is simpler in actual practice and gives results of acceptable accuracy. It appears that stem taper is a surrogate measurement for stress wave velocity and provides similar information.

It is an object of the present invention to provide a method that has reliable predictive power indicating which logs might produce low strength or warp prone lumber.

It is another object to provide a method that uses log taper and may include other log geometric parameters in combination with taper to indicate logs that might produce low strength or warp prone lumber.

It is a further object to create multivariate regression equations with log taper and other log geometric parameters as independent variables predictive of low strength or warp prone lumber.

These and many other objects will become readily apparent to those skilled in the art upon reading the following detailed description taken in conjunction with the drawings.

BRIEF DESCRIPTION OF THE DRAWINGS

FIGS. 1–5 show various types of warp that can occur in sawn lumber.

DETAILED DESCRIPTION OF THE PREFERRED EMBODIMENTS

Warp in lumber is believed caused by a number of growth factors that cause differential longitudinal or radial shrinkage in the trees from which the lumber is produced. Compression or tension wood produced to overcome stress unbalances experienced by the trees during growth is one factor that affects warp. Compression wood in a tree may have a high microfibril angle, also known as a cause of warp. Spiral grain is an additional warp-causing factor. Conifers typically have a generally cylindrical core portion of so-called juvenile wood about 10–15 annual rings wide that will be of higher microfibril angle and lower density than the wood formed later. This wood also tends to have a higher longitudinal shrinkage than the wood produced later so that a radial shrinkage gradient is established across the tree stem. Microfibril angle and wood density are directly related to stiffness. A tree having higher microfibril angle and lower density wood will typically produce weaker lumber than one of the same species having lower microfibril angle and higher density.

Warp in lumber assumes several forms that may be present singly or in combination. As seen in FIGS. 1 and 2, crook and bow are the result of differential longitudinal shrinkage in various portions of sawn lumber. One must differentiate between "longitudinal shrinkage" which is measured parallel to the fiber direction, and "lengthwise shrinkage" which is measured parallel to the longitudinal axis of the board (FIG. 3). These may or may not be the same. Cup, shown in FIG. 4, is principally the result of variations in tangential shrinkage which tends to increase as one moves radially outward from the pith. Twist, as illustrated in FIG. 5, is normally the result of spiral grain in the log from which the lumber was sawn.

Figure 6:
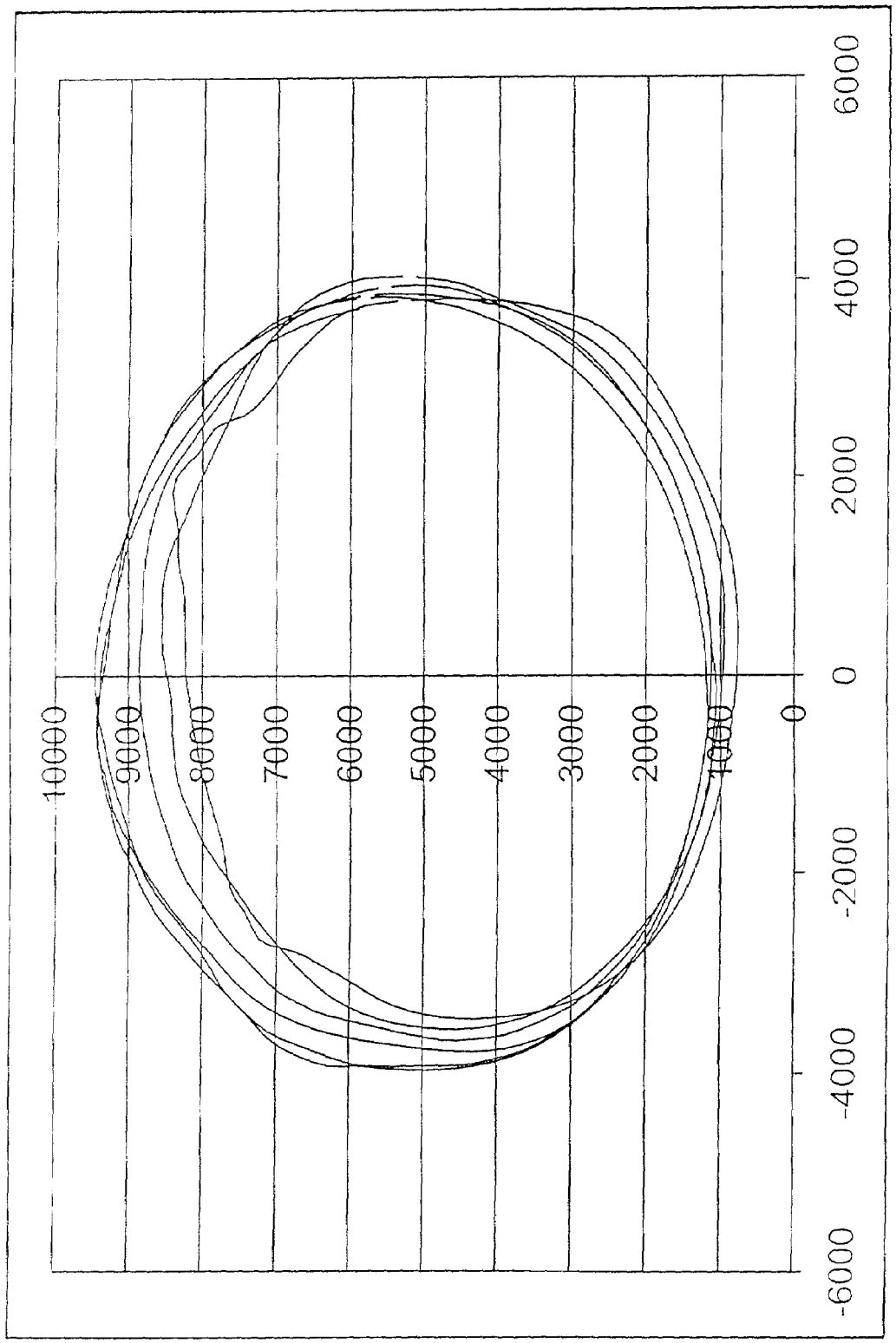
FIGS. 6 and 7 show actual superposed circumferential scans along the lengths of two logs having different geometric configurations.
Figure 7:
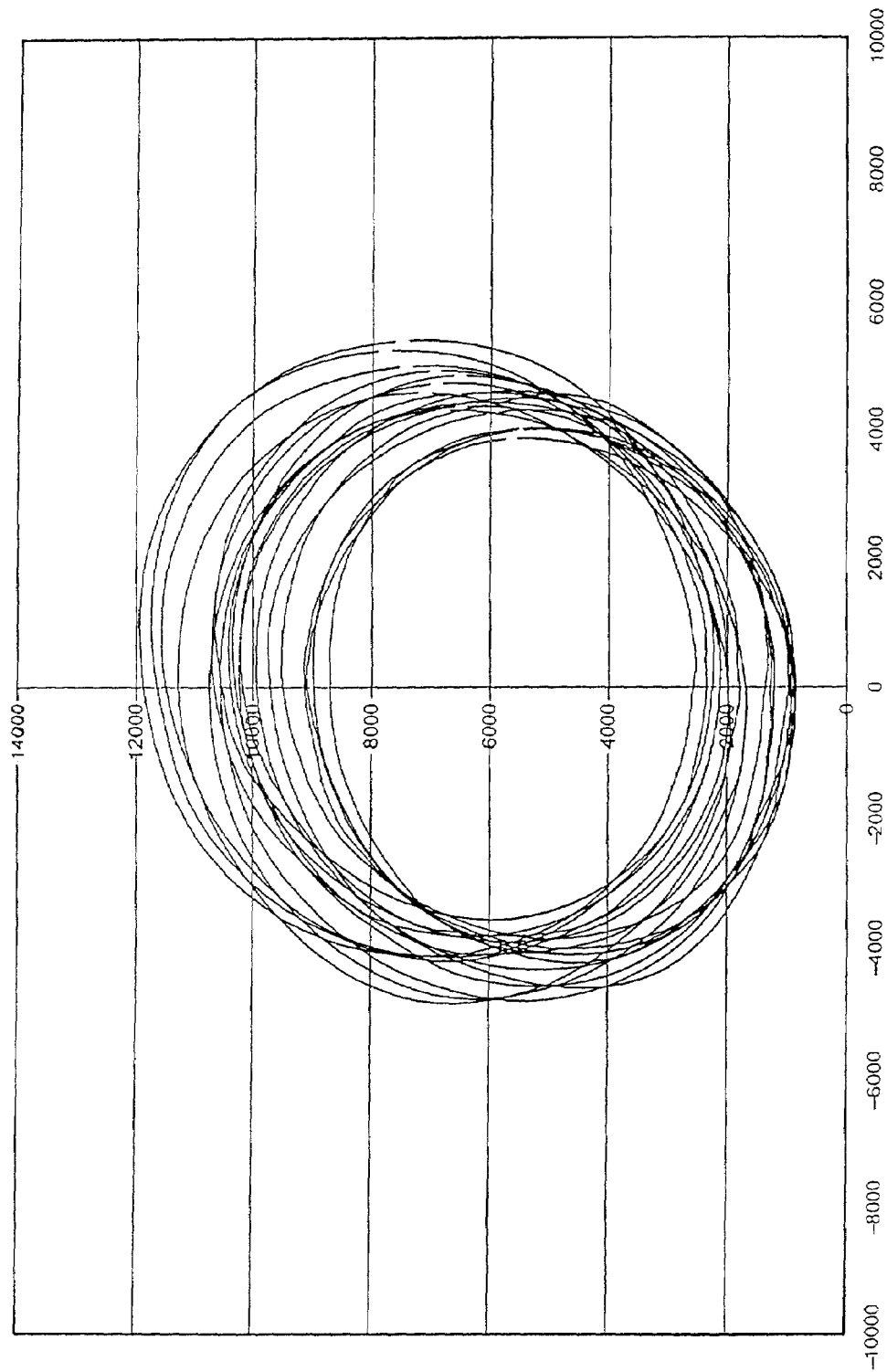

The days in which a highly skilled head sawyer made real time decisions as to how a log should be optimally cut have largely passed with the near disappearance of the huge old growth logs from the nation's forests. Automation in sawmilling is now a fact of life for most but the smallest mills. The smaller logs now grown in tree farms must be processed at dazzling rates in order for mills to be competitive. Scanners and computers now make most of the decisions formerly made by the head sawyer. Logs are now typically scanned for size and geometric configuration one or more times before they approach the head saw or primary processing center. This may occur in a sort yard or merchandiser that makes an initial determination of the best use for the log. The log may be scanned again as it enters a sawmill. A typical scanner will make multiple determinations of the log circumference at short intervals along the length. These measurements will denote log diameter, length, and taper, as well as longitudinal sweep and any cross section eccentricity. FIG. 6 shows six superposed scans of a log having little sweep and a generally round, although irregular, cross section. FIG. 7 illustrates eighteen superposed scans along a log having a somewhat elliptical cross section and significant sweep. Vertical and horizontal scales of these figures differ somewhat and distort the apparent cross sections. Scales shown on these figures are arbitrary. It can be presumed that the y axis is vertical and the x axis horizontal. The scanners are generally based on a battery of laser distance measuring cameras that perform the task without log rotation. Information from the scanners is entered into a computer programmed to automatically determine the best orientation of the log as it enters the primary breakdown saw. The log will then be automatically rotated through the desired angle relative to its position when scanned. The computer will also set the saws for the initial cuts to get the maximum lumber value from the log.

As was noted earlier, stress wave velocity of logs is very useful in prediction of structural properties of lumber cut from the log. However, this is not generally a convenient measurement to make. It is particularly difficult in many mills where space at the green (or log input) end is limited. It becomes particularly inconvenient where probes must be inserted into or even placed in contact with opposite ends of a log. A simpler measurement, or at least one more convenient to make without necessitating major mill revisions or procedural changes, would enable much wider application for prediction of lumber properties.

Figure 8:
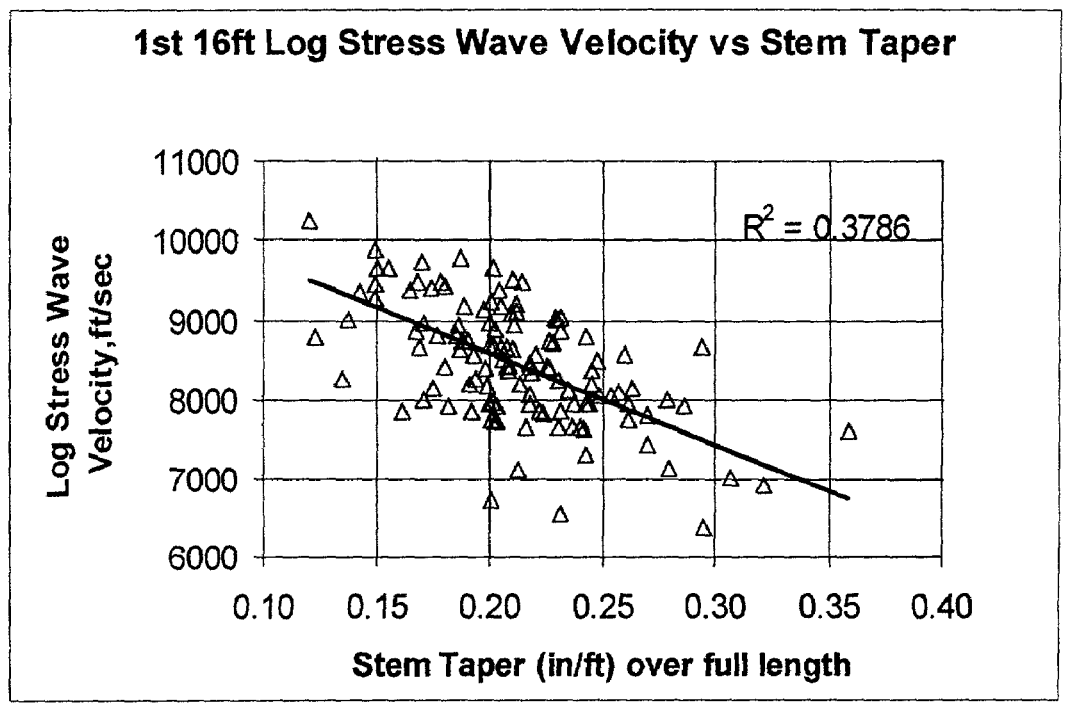
FIG. 8 is a plot showing the relationship between stress wave velocity and log taper.

FIG. 8 shows a plot of stress wave velocity against log taper for a large sample of logs. A linear relationship is seen suggesting that taper may be used as a surrogate measurement for stress wave velocity.

While it appears that lumber warp such as crook or bow was related in some way to stress wave velocity there apparently were other more important factors unaccounted for. Similarly, in the past, tree geometry by itself has been believed to be a relatively poor predictor of lumber warp propensity. This has been the case even though asymmetry in cross section or non-linearity of the longitudinal axis would suggest the presence of compression wood known to have different shrinkage characteristics that would affect lumber warp. The present invention shows that log taper alone or in combination with other geometric measurements is useful in predicting warp propensity and stiffness of lumber cut from the logs.

EXAMPLE 1

A sawing study was conducted in which 80 loblolly pine plantation trees from three Arkansas stands were harvested, and the first two 16+ foot (4.88 m) lengths were sawn into nominal 2 inch dimension lumber in nominal 4–12 inch widths. The three stands ranged in age from 20 to 24 years old and the trees averaged 10.5 inches (267 mm) in diameter at breast height. The useful tree stem length would typically be in the range of about 38–42 ft (12.8 m) with a 6 in (15 cm) top diameter. Taper measurements potentially correlated with lumber stiffness and warp were made on the full stem length log, the first 32 feet, and the first 16 feet. The tree length and 33 foot taper measurements were made by hand and the 16 foot taper was measured by the mill log scanner. Taper was determined by subtracting the average diameter at the upper end from the average lower end diameter and dividing by log length. All processed lumber was coded to relate to the tree from which it was sawn. The test lumber was kiln dried and graded according to normal mill practice. After grading, several test sizes were retrieved for warp evaluation. These sizes included nominal 2×4s in 12 and 16 foot lengths, 2×6s in 14 and 16 foot lengths, and 2×8s in 12 and 16 foot lengths. The data set included trees that resulted with at least three pieces of lumber for which MOE and warp measurements were made. Warp measurements were made on these pieces using methods detailed by the Southern Pine Inspection Bureau lumber grading standards. Stiffness was measured in the plank mode by a commercially available dynamic MOE (vibration) machine. Average warp and MOE of all pieces cut from an individual tree was then computed.

Figure 9:
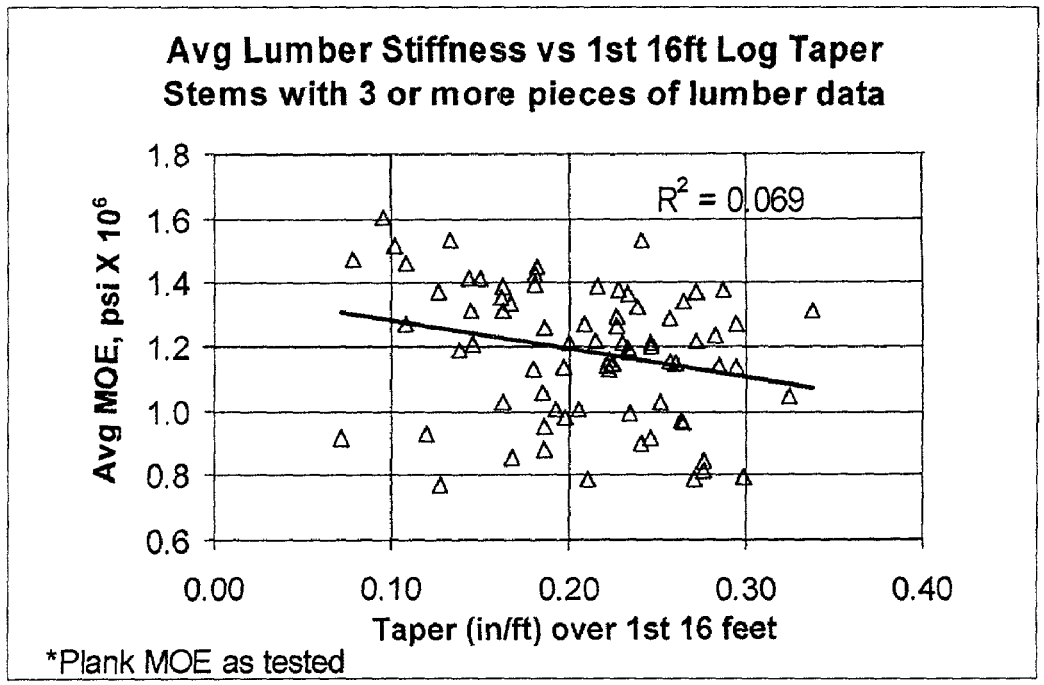
FIGS. 9–11 are graphs showing the relationship between lumber stiffness and log taper for three log lengths.
Figure 10:
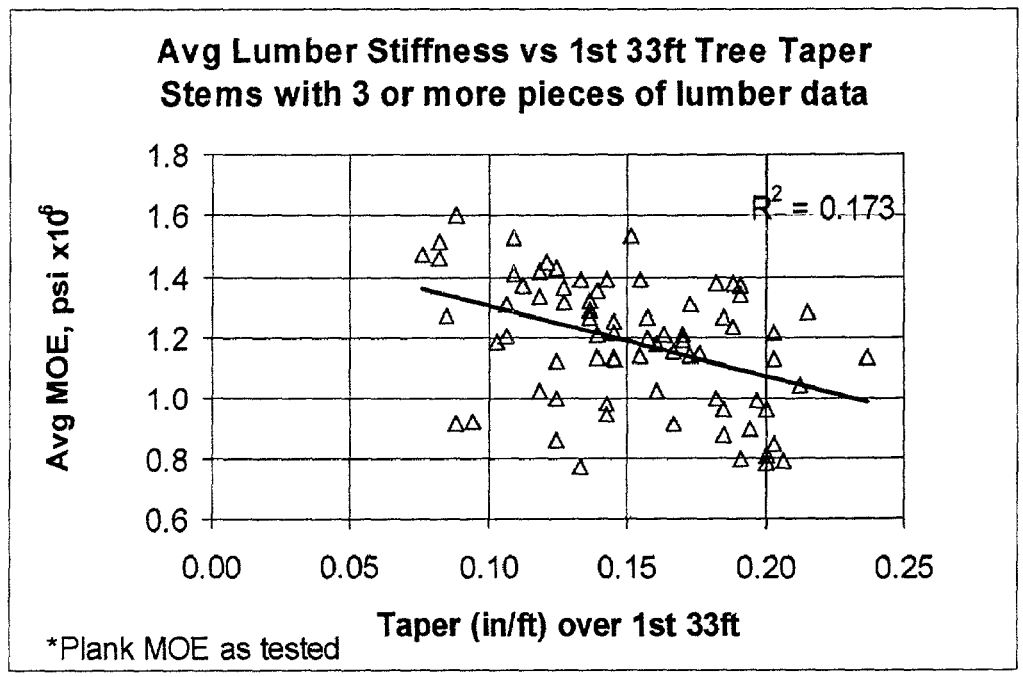
Figure 11:
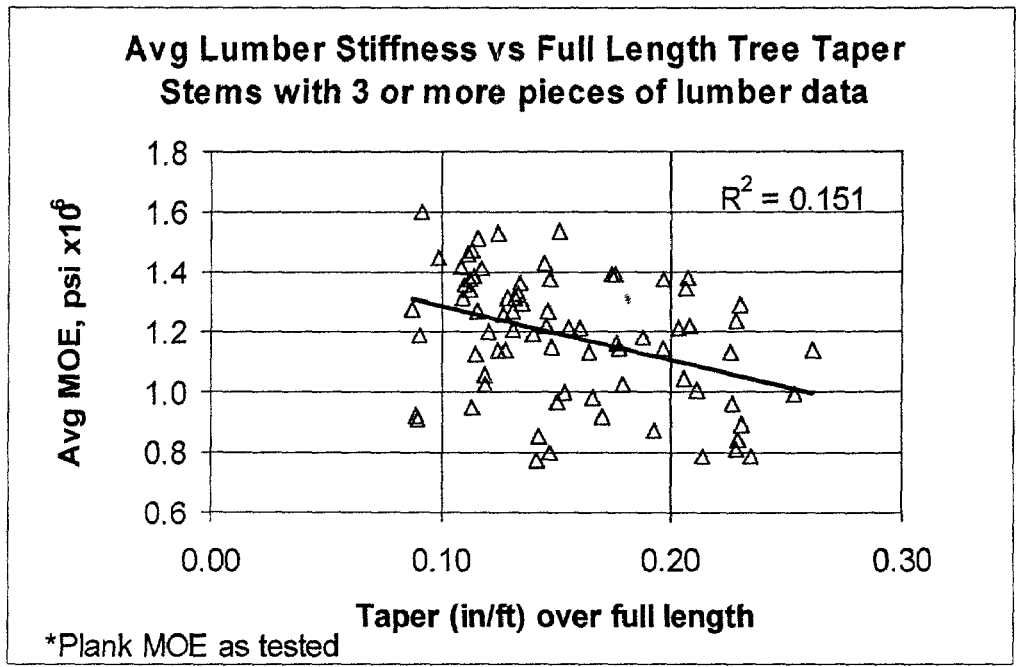
Figure 12:
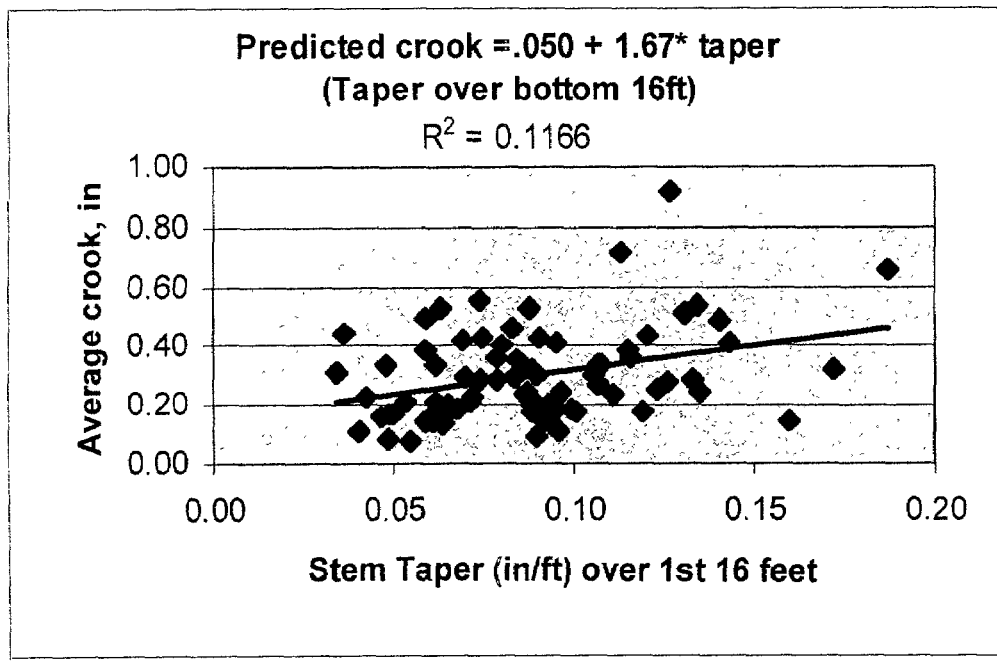
FIGS. 12–14 are graphs showing the relationship between lumber crook and log taper for three log lengths.
Figure 13:
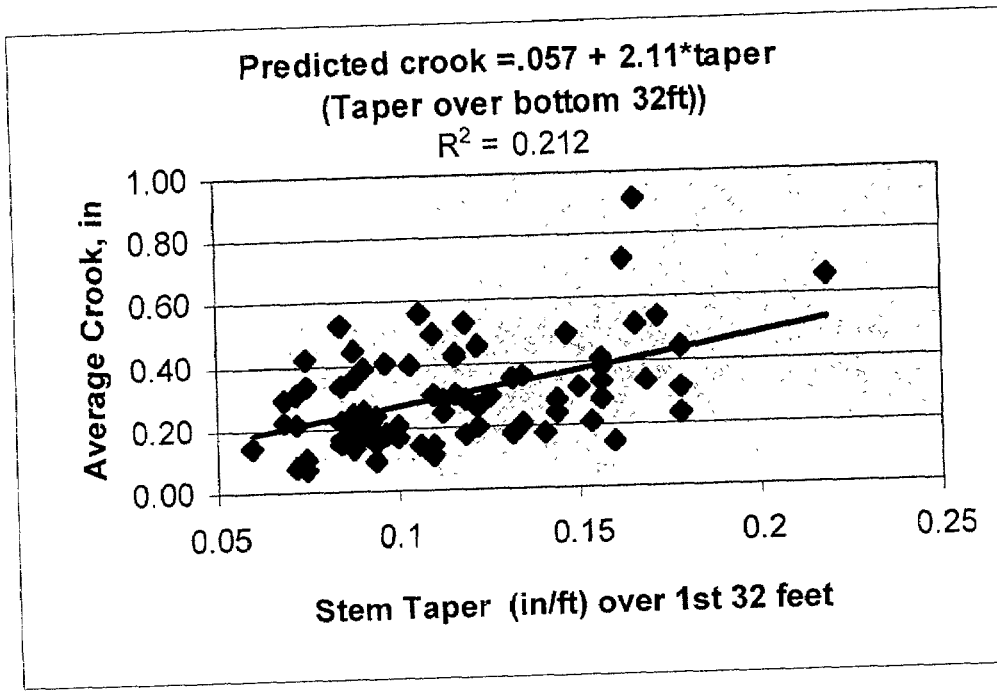
Figure 14:
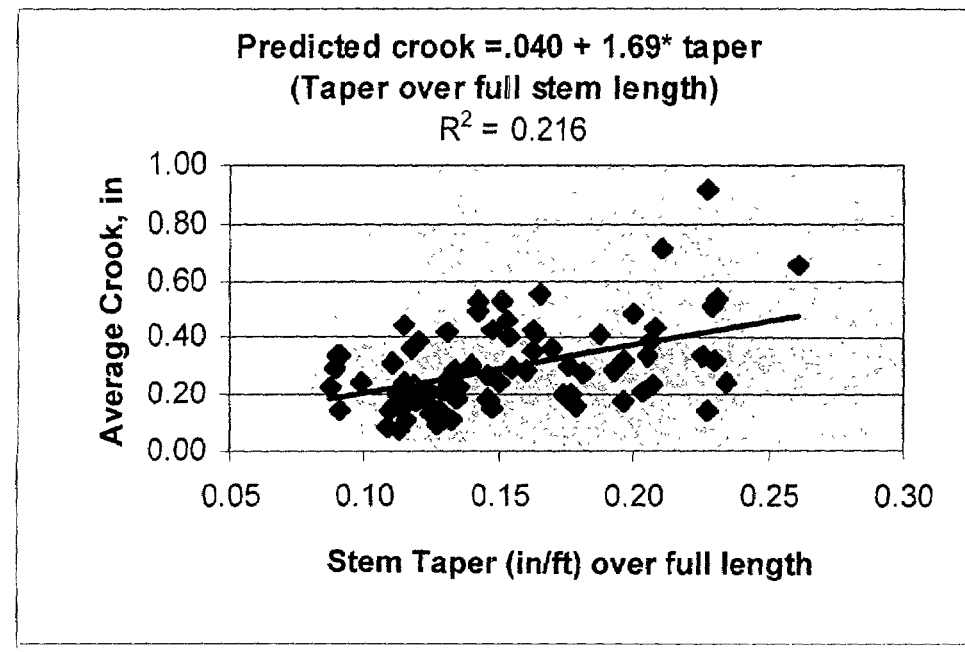

The relationship between taper and modulus of elasticity (stiffness) is shown in FIGS. 9–11. In this test, correlation is generally poor between these parameters for the first 16 ft log (FIG. 9). However, it improves significantly and becomes a useful predictor when the taper is measured over the longer lengths, as seen in FIGS. 10 and 11. The lumber that was measured was taken from any of the logs cut from the tree In similar fashion, the relationship between taper and lumber crook for this data set is shown in FIGS. 12–14. Again the relationship ($R^2$) is weakest between the taper of the first log and crook (FIG. 12) but increases as the log length measured is increased (FIGS. 13 and 14).

The predictive relationship between taper and crook is improved if other geometric factors are included in a multivariate regression equation. This is seen in the following example based on the same data set as above.

EXAMPLE 2

As each log approached the primary breakdown center in the sawmill, geometric data were generated by the Perceptron Log Optimizer software using four TriCam laser scanners. This equipment, manufactured by Perceptron Forest Products Division, Atlanta Ga., is typical of many of the scanners used in sawmills. Scanners used at this location will normally determine the best log orientation entering the saw and the optimum saw settings. In the present test the scanners measured x-y coordinates at about 100 points around the circumference of the log at each 1 ft (305 mm) increment along the log (refer to FIGS. 6 and 7 as examples). The x values and y values of each circumferential scan were averaged to determine a center point location. A longitudinal line is chosen as a reference location. Sixteen additional measurements potentially correlating to lumber warp were derived from the scanning data.

A. Major axis sweep (in).
B. Minor axis sweep (in).
C. Combined sweep (in).
D. Maximum x change (in).
E. Average x change (in).
F. Standard deviation of x change.
G. Maximum y change (in).
H. Average y change (in).
I. Standard deviation of y change.
J. Average major diameter (in).
K Standard deviation of major diameters.
L. Average minor diameter (in).
M. Standard deviation of minor diameters.
N. Maximum eccentricity (in).
O. Average eccentricity (in).
P. Standard deviation of eccentricity.

Sweep typically will predominantly lie in a single plane but may be more complex. The scanner was programmed to determine the predominant plane and a minor plane of sweep, if one existed. Sweep in the predominant plane was designated the major axis sweep. Combined sweep was determined by taking the square root of the sum of the squares of the major axis and minor axis sweep measurements.

Maximum x change was calculated by taking the largest difference between the values of the x center locations of adjacent cross sections. Maximum y change was similarly calculated. Averages and standard deviations were determined using data from all sections. These measurements again relate to sweep.

Major diameter is the largest diameter and the minor diameter the smallest diameter computed at each cross section. Eccentricity is computed as the square root of the difference between the squared major diameter dimension and the square of the minor diameter dimension for each scanned section. The average eccentricity is determined from all cross sections and the maximum from the greatest eccentricity measured in a single section.

Each of the variables studied was analyzed using a multiple linear regression program to see which factors singly or in combination, if any, correlated with measured lumber warp. Many such statistical analysis programs are readily available as commercial products or in the public domain. The scanner determined variables were studied for just the first 16 foot log. Statistical significance of the important variables is seen in Table 1.

TABLE 1

Variables Correlating with Average Lumber Crook

| Variable | $R^2$ | P Value |
|---|---|---|
| Average y change | 0.25 | 2.03E-06 |
| Taper (1–32 ft) | 0.216 | 1.61E-05 |
| Maximum y change | 0.17 | 0.00016 |
| Standard deviation y change | 0.13 | 0.0014 |
| Combined sweep | 0.11 | 0.003 |
| Standard deviation major diameter | 0.11 | 0.003 |

Figure 15:
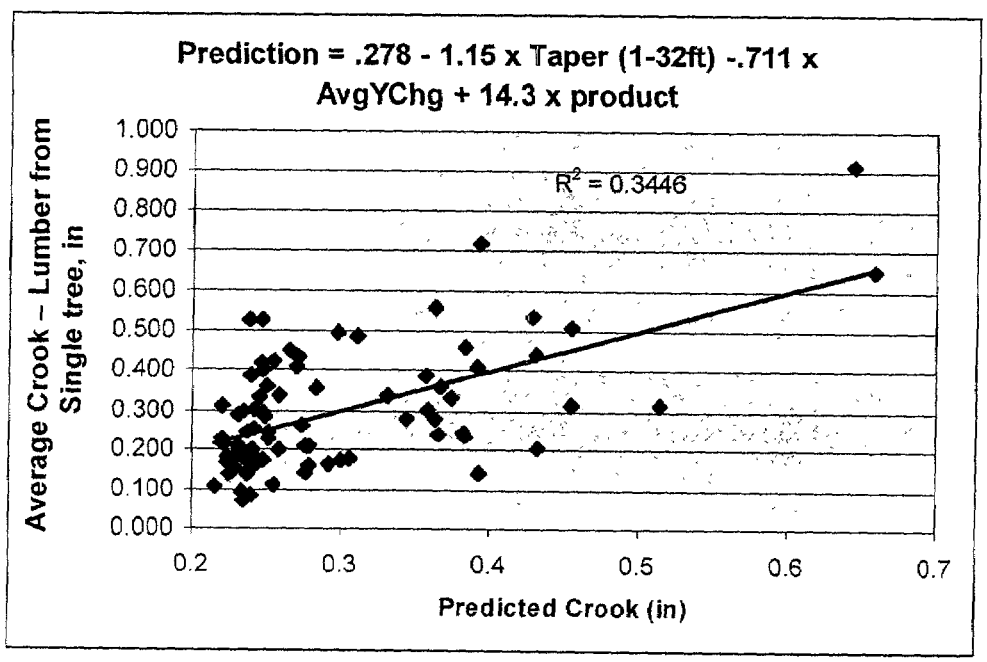
FIG. 15 is a similar graph to those of the immediately preceding figures which further includes a measure of log crook as an independent variable, along with taper.

It should be noted that four of the above variables, excluding taper and butt diameter, are related to log sweep. By combining average y change with taper the $R^2$, indicative of predictive probability, is increased from 0.22 to 0.34. This is seen in the graph plotted in FIG. 15. It can be presumed that the predictive power for estimating lumber stiffness will be similarly increased by including other geometric parameters along with crook.

EXAMPLE 3

Figure 16:
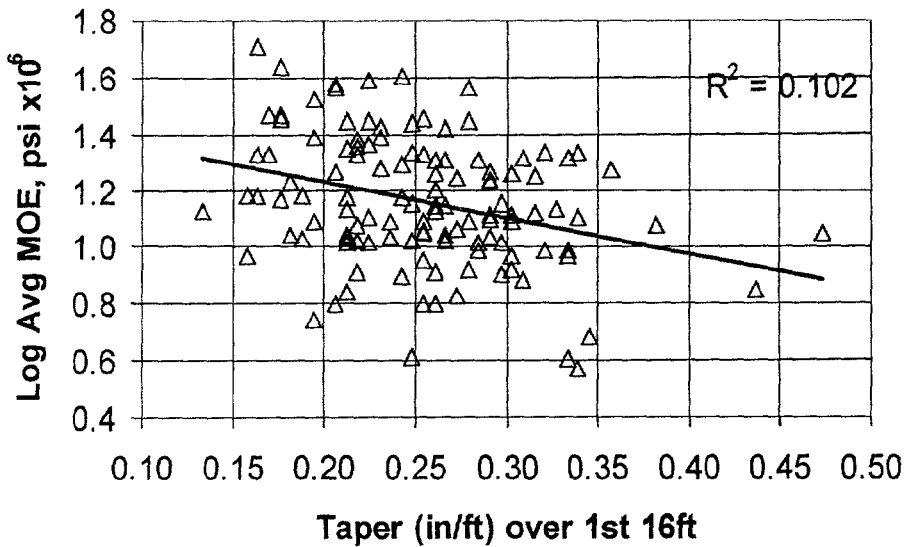
FIGS. 16 and 17 are graphs from another test showing the relationship between lumber stiffness and log taper of two log length.
Figure 17:
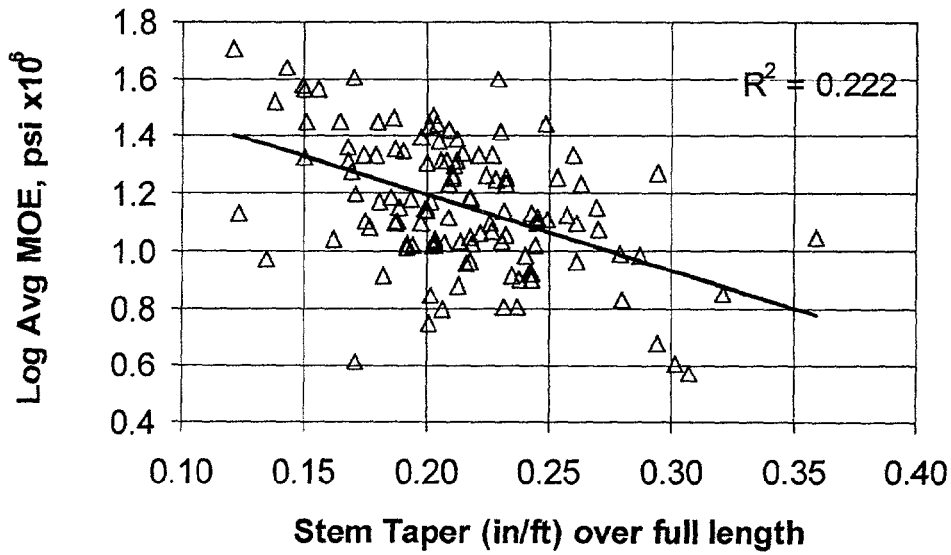

A second study was made on mid-south (Dierks, Ark.) loblolly pine lumber using about 120 trees. These were from a second thinning harvest and were approximately 26 years old. Full length stem taper and the 16 foot butt (first) log taper were measured as just described. Stress wave velocity was measured similarly for the full length stem and 16 foot (4.88 m) logs. The butt logs were sawn, and the lumber measured for MOE in the joist mode. In this case lumber was marked so as to be traceable back to both the tree and the log from which it was cut. The results of first log stress wave velocity plotted against taper of the full length tree stem is shown in FIG. 8. Results of taper vs MOE are shown in FIGS. 16 and 17. The correlation between taper and stiffness is substantially higher than in the previous test, both for first log taper and full stem length taper. Again, taper is seen as a useful predictor of lumber strength. This enables decisions as to optimum log utilization to be made both in the sort yard and as the log enters the sawmill.

EXAMPLE 4

The use of taper as a stiffness predictor is equally applicable to veneer as it is to lumber. Many lumber-like products are now manufactured from parallel laminated veneers. These products are used where high and predictable strengths are needed, such as truss chords. Similarly, there is a market for premium plywood products made with high strength veneers.

Figure 18:
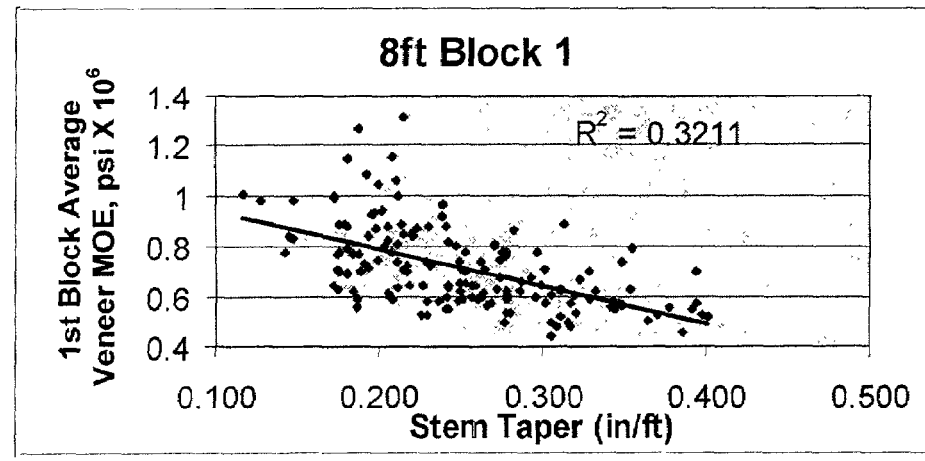
FIGS. 18–23 are graphs showing the relationship of veneer stiffness and log or lathe block taper.
Figure 19:
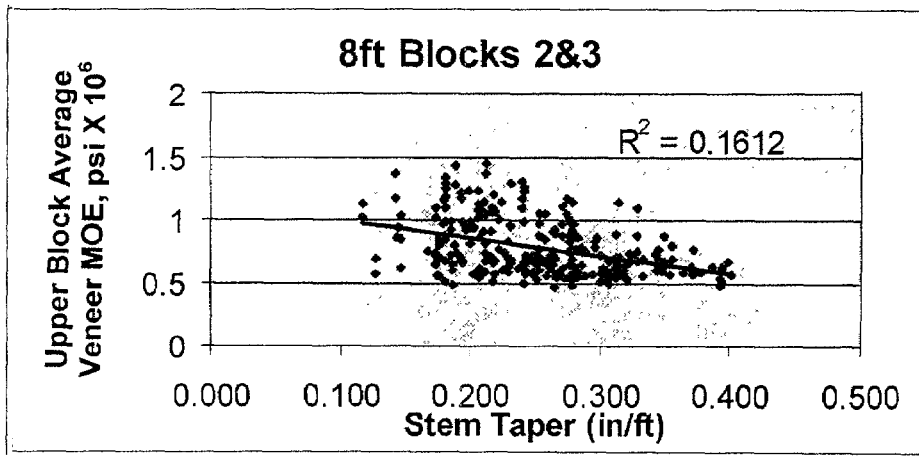
Figure 20:
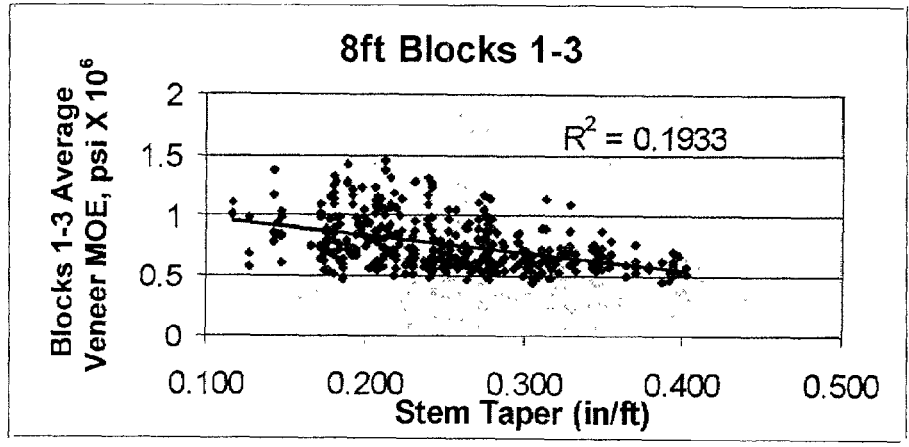
Figure 21:
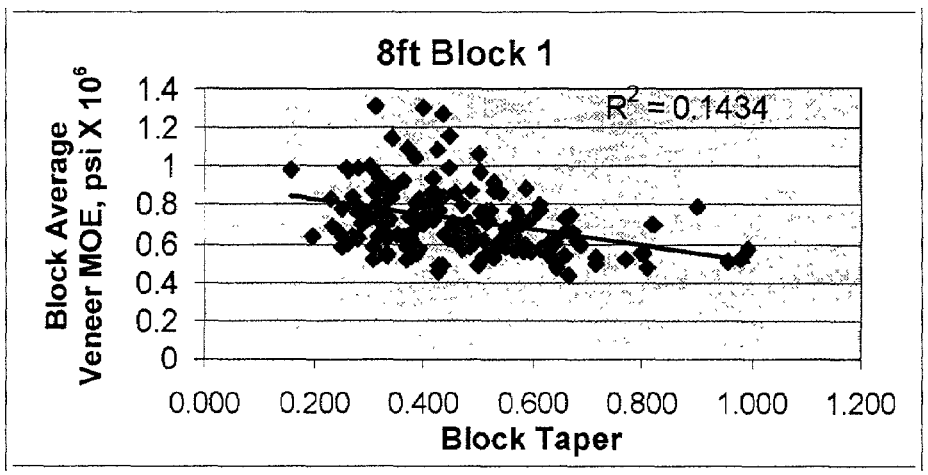
Figure 22:
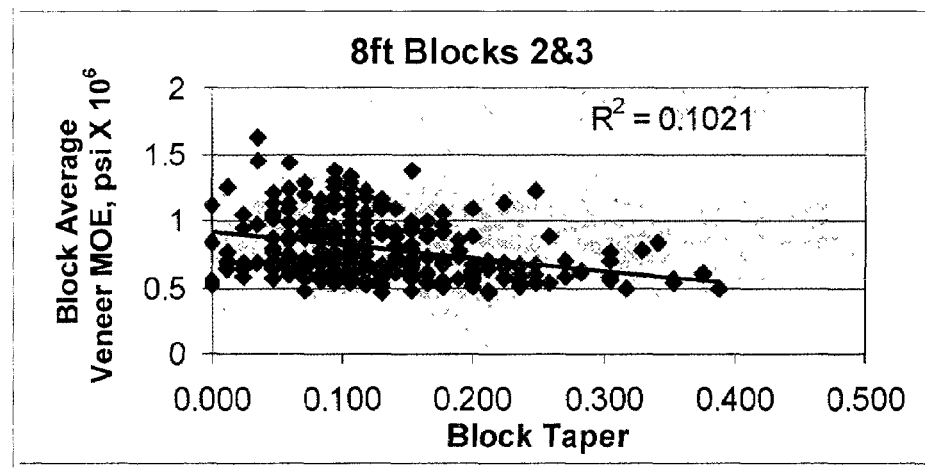
Figure 23:
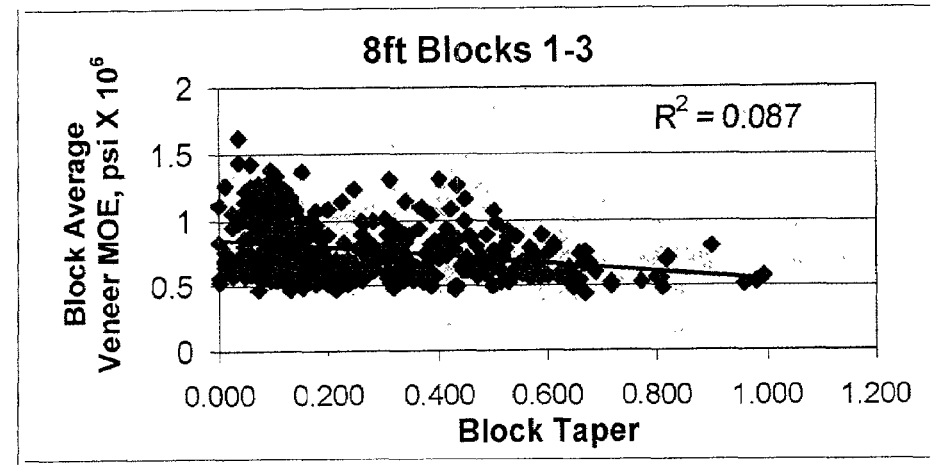

In a study of about 170 loblolly pine second thinning trees (approximately 24 years old), veneer from the first three 8 foot (2.44 m) lathe blocks was analyzed for stiffness and the results correlated with log geometric properties. There were about 170 butt blocks and 275 upper blocks (second, and third in some cases). The full length taper of each harvested stem was measured as was the taper of each lathe block. All full sheet veneer from each block was recovered and the dry weight, volume, and stress wave velocity of each sheet was measured. From these measurements the MOE of each sheet was estimated using the well known relationship $MOE=\rho V^2$, where $\rho$ is mass density and V is stress wave velocity. Results using stem taper as the predictor of MOE are shown in FIGS. 18–20. A very good correlation exists between full length stem taper and the butt (or first) block stiffness as seen in FIG. 18. The correlation is somewhat lower for the upper blocks or when all three blocks are combined (FIGS. 19 and 20). As seen in FIGS. 21–23 the correlation falls off when the taper of each individual block is used as the predictor. Again it is best for the butt block (FIG. 21). As was seen with the prediction of warp propensity in the first example, inclusion of other log geometric measurements along with taper would be expected to improve the predictive power for estimating veneer stiffness.

It is readily apparent that knowledge of tree or log taper is a simple and effective predictor of properties such as lumber crook or of lumber or veneer stiffness in material produced from any given log. It will be evident to those skilled in the art that many variations can be made in the present invention that have not been specifically exemplified. These should be considered to be within the scope of the invention if encompassed within the following claims.

We claim:

1. A method of predicting properties of lumber or veneer produced from a given log from a log which comprises:
   sampling a representative group of logs of a common species and establishing a regression equation by correlating log taper with observed structural properties or warp of lumber milled from the representative group of logs;
   measuring taper of an individual log chosen from outside said representative group; and
   entering the taper of the individual log into the regression equation to predict structural properties or warp propensity of lumber or veneer that might be produced from the log.

2. The method of claim 1 in which taper is measured on a standing tree before harvest.

3. The method of claim 1 in which the taper is measured over the full stem length of a log after harvest.

4. The method of claim 1 in which taper is measured over any segment of a tree stem.

5. The method of claim 1 in which the taper is measured over the length of a log cut to a veneer block.

6. The method of claim 1 in which the taper is measured over the 25 length of a log cut to a length for sawing into lumber.

7. The method of claim 1 in which the property predicted is wood stiffness.

8. The method of claim 1 in which the property predicted is warp of lumber sawn from the log.

9. The method of claim 1 that further includes incorporation of additional log external geometric data along with taper.

10. The method of claim 9 in which the additional log geometric data is related to measurements indicating any departure from axial linearity.

11. The method of claim 9 in which the additional log geometric data is related to measurements indicating any departure from circularity of cross section.

12. The method of claim 9 in which the additional log geometric data is related to measurements indicating both any departure from axial linearity and those indicating any departure from circularity of cross section.

13. A method of predicting properties of lumber or veneer produced from a given log from a log which comprises:
- sampling a representative group of logs of a common species and establishing a multivariate regression equation by correlating log taper and at least one additional geometric measurement of the logs with observed warp of lumber milled from the representative group of logs, the additional geometric measurement or measurements indicating at least deviations from axial linearity;
- measuring taper of an individual log chosen from outside said representative group;
- measuring geometric configuration of the individual log to determine at least any deviation from axial linearity; and
- entering the taper and at least one additional geometric measurement into the regression equation to predict warp propensity of lumber that might be sawn from the individual log.

14. The method of claim 13 in which the log geometric configuration is determined by multiple scans to establish a plurality of circumferential configurations along the log length, each configuration being determined by measurement of multiple points around the log circumference, the scans being made orthogonal to a longitudinal reference line generally parallel to the log, the circumferential configurations being indicative of the log cross sections and their displacement from the reference line at the scan location.

15. The method of claim 14 in which the points determining the circumferential configurations defining the cross sections are projected relative to a pair of mutually orthogonal axes, arbitrarily called the x and y axes, and the average x and y values are determined to indicate a centerpoint location relative to the longitudinal reference line for each individual circumferential configuration.

16. The method of claim 15 in which the reference line is arbitrarily assigned as a z axis, the circumferential configurations defining the cross sections are placed in their proper relation and sequential location relative to the z axis, and displacement of the center points from the z axis are determined in order to estimate major and minor sweep axes of the log.

17. The method of claim 15 in which the average changes of the y center location coordinates are determined by calculating the differences between all adjacent cross section center point locations along the log length and averaging the values.

18. The method of claim 17 in which taper and at least measurements indicating average change of the y center coordinates are included as independent variables in the multivariate regression equation predicting lumber crook.

* * * * *